US00PP15244P2

(12) United States Plant Patent
Heffner

(10) Patent No.: US PP15,244 P2
(45) Date of Patent: Oct. 19, 2004

(54) **MINI *IMPATIENS* PLANT NAMED 'BODLIZSAL'**

(50) Latin Name: *Impatiens walleriana*
Varietal Denomination: Bodlizsal

(75) Inventor: Michael R. Heffner, Santa Barbara, CA (US)

(73) Assignee: John Bodger + Sons Company, South El Monte, CA (US)

( * ) Notice: Subject to any disclaimer, the term of this patent is extended or adjusted under 35 U.S.C. 154(b) by 0 days.

(21) Appl. No.: 10/742,979

(22) Filed: Dec. 22, 2003

(51) Int. Cl.[7] ..... A01H 5/00
(52) U.S. Cl. ..... Plt./317
(58) Field of Search ..... Plt./317

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Mini *Impatiens* plant named 'Bodlizsal', characterized by its compact, upright, outwardly spreading and mounded plant habit; freely branching habit; dense and bushy growth habit; small dark green-colored leaves; freely flowering habit; and small dark pink-colored flowers that are positioned above and beyond the foliage.

1 Drawing Sheet

Botanical classification/cultivar designation: *Impatiens walleriana* cultivar Bodlizsal.

BACKGROUND OF THE INVENTION

The present Invention relates to a new and distinct cultivar of Mini *Impatiens* plant, botanically known as *Impatiens walleriana,* and hereinafter referred to by the name 'Bodlizsal'.

The new Mini *Impatiens* is a product of a planned breeding program conducted by the Inventor in Lompoc, Calif. The objective of the breeding program was to develop new compact and freely-branching Mini *Impatiens* cultivars with numerous small flowers and attractive flower and foliage coloration.

The new *Impatiens* originated from a self-pollination made by the Inventor in December, 1999, of a proprietary *Impatiens walleriana* selection identified as code number 01IM240-2, not patented. The cultivar Bodlizsal was discovered and selected by the Inventor as a flowering plant within the progeny of the stated self-pollination in a controlled environment in Lompoc, Calif.

Asexual reproduction of the new cultivar by terminal cuttings in Lompoc, Calif., has shown that the unique features of this new *Impatiens* are stable and reproduced true to type in successive generations of asexual reproduction.

SUMMARY OF THE INVENTION

The following traits have been repeatedly observed and are determined to be the unique characteristics of 'Bodlizsal'. These characteristics in combination distinguish 'Bodlizsal' as a new and distinct Mini *Impatiens* cultivar:

1. Compact, upright, outwardly spreading and mounded plant habit.
2. Freely branching habit; dense and bushy growth habit.
3. Small dark green-colored leaves.
4. Freely flowering habit.
5. Small dark pink-colored flowers that are positioned above and beyond the foliage.

Plants of the new *Impatiens* differ primarily from plants of the parent selection in the following characteristics:

1. Plants of the new *Impatiens* are more compact than plants of the parent selection.
2. Plants of the new *Impatiens* have smaller leaves than plants of the parent selection.
3. Plants of the new *Impatiens* have smaller flowers than plants of the parent selection.
4. Flowers of plants of the new *Impatiens* are dark pink in color whereas flowers of plants of the parent selection are coral pink in color.

The new *Impatiens* can be compared to the *Impatiens walleriana* cultivar Fify Salmon, disclosed in U.S. Plant Pat. No. 11,559. However, in side-by-side comparisons conducted in Lompoc, Calif., plants of the new *Impatiens* differed from plants of the cultivar Fify Salmon in the following characteristics:

1. Plants of the new *Impatiens* were taller than plants of the cultivar Fify Salmon.
2. Plants of the new *Impatiens* were more freely branching than plants of the cultivar Fify Salmon.
3. Plants of the new *Impatiens* had larger leaves than plants of the cultivar Fify Salmon.
4. Plants of the new *Impatiens* had larger flowers than plants of the cultivar Fify Salmon.
5. Plants of the new *Impatiens* had lighter pink-colored flowers than plants of the cultivar Fify Salmon.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Impatiens.*

The photograph at the top of the sheet comprises a side perspective view of a flowering plant of 'Bodlizsal'.

The photograph at the bottom of the sheet is close-up view of typical flowers and leaves of 'Bodlizsal'.

DETAILED BOTANICAL DESCRIPTION

Plants of the cultivar Bodlizsal have not been observed under all possible environmental conditions. The phenotype may vary somewhat with variations in environment such as temperature and light intensity, without, however, any variance in genotype. The aforementioned photographs and following observations and measurements describe plants grown in Lompoc, Calif., under commercial practice in a polycarbonate-covered greenhouse during the winter and spring with day temperatures ranging from 18 to 24° C., night temperatures ranging from 16 to 18° C. and light levels ranging from 4,000 to 8,000 foot-candles. Rooted young plants were planted in 10-cm containers and had been growing for about 16 weeks when the photographs and the description were taken. In the following description, color references are made to The Royal Horticultural Society Colour Chart, 1995 Edition, except where general terms of ordinary dictionary significance are used.

Botanical classification: *Impatiens walleriana* cultivar Bodlizsal.

Parentage: Self-pollination of a proprietary *Impatiens walleriana* selection identified as code number 01IM240-2, not patented.

Propagation:

*Type cutting.*—Terminal cuttings.

*Time to initiate roots.*—About 14 days at 22° C.

*Time to produce a rooted young plant.*—About 28 days at 20° C.

*Root description.*—Fine, fleshy; white in color.

*Rooting habit.*—Freely branching.

Plant description:

*General appearance.*—Compact, upright, outwardly spreading and mounded plant habit.

*Growth and branching habit.*—Moderately vigorous and freely-branching growth habit with about 17 basal branches; lateral branches potentially forming at every node; dense and bushy growth habit. Pinching, that is removal of the terminal apex, is typically not required, but will enhance branching.

*Plant height.*—About 12 cm.

*Plant diameter or spread.*—About 37 cm.

*Lateral branches.*—Length: About 17 cm. Diameter: About 5 mm. Internode length: About 1.5 to 2 cm. Texture: Smooth, glabrous. Color: 148C with random flecks, 185C.

*Foliage description.*—Arrangement: Alternate, simple. Length: About 3.5 cm. Width: About 2.2 cm. Shape: Elliptical. Apex: Acute. Base: Attenuate. Margin: Slightly crenate with ciliation. Texture, upper and lower surfaces: Smooth, glabrous. Venation pattern: Pinnate. Color: Developing and fully expanded foliage, upper surface: 147A. Developing and fully expanded foliage, lower surface: 147B. Venation, upper surface: 147C. Venation, lower surface: 147D.

Petiole: Length: About 2 cm. Diameter: About 2 mm. Texture, upper and lower surfaces: Smooth, glabrous. Color: 147D.

Flower description:

*Flower type and habit.*—Numerous small single flowers that are roughly triangular in shape. Four to five flowers arranged in axillary clusters. Freely flowering, usually about 35 flowers and flower buds per lateral branch. Flowers positioned above the foliage and typically face upright or outward. Flowers last about five to seven days under greenhouse conditions. Flowers persistent. Flowers not fragrant.

*Natural flowering season.*—Flowering is continuous through the spring and summer.

*Flower size.*—Height: About 3 cm. Width: About 2.6 cm. Depth (not including spur): About 1.6 cm.

*Flower buds* (*at stage of showing color*).—Length: About 1 cm. Diameter: About 5 mm. Shape: Ovoid. Color: 52D.

*Petals.*—Quantity/arrangement: Five per flower in a single whorl. Length, banner petal: About 1 cm. Length, lateral petals: About 1.2 cm. Length, basal petals: About 1.7 cm. Width, banner petal: About 1.3 cm. Width, lateral petals: About 8 mm. Width, basal petals: About 9 mm. Shape: Obovate to slightly cordate. Apex: Rounded and slightly emarginate. Base: Attenuate. Margin: Entire. Texture, upper and lower surfaces: Smooth, glabrous. Color: When opening, upper surface: 50A. When opening, lower surface: 51D. Fully opened, banner and lateral petals, upper surface: 50A. Fully opened, basal petals, upper surface: 50A; towards the base, 61A. Fully opened, lower surface: 52C.

*Sepals.*—Quantity/arrangement: Five in a single whorl; one modified into an elongated spur. Calyx length: About 5 mm. Calyx diameter: About 5 mm. Shape: Elliptic. Apex: Acute. Margin: Entire. Texture, upper and lower surfaces: Smooth, glabrous. Color, upper and lower surfaces: Close to 144A. Spur length: About 2.7 cm. Spur diameter: At flower, about 2 mm; at apex, less than 1 mm. Spur color: 54C.

*Peduncles.*—Length: About 1.5 cm. Diameter: About 2 mm. Angle: About 45° from vertical. Strength: Strong. Texture: Smooth, glabrous. Color: 146B.

*Reproductive organs.*—Stamens: Quantity: Five fused around stigma. Anther length: About 3 mm. Anther color: 51B. Pollen amount: Scarce. Pollen color: 51A. Pistils: Quantity per flower: One. Pistil length: About 3 mm. Stigma shape: Rounded. Stigma color: 61A. Style color: 137A. Ovary color: 137A.

*Seed/fruit.*—Seed and fruit production have not been observed.

Disease/pest resistance: Plants of the new *Impatiens* have not been observed to be resistant to pathogens and pests common to *Impatiens*.

It is claimed:

1. A new and distinct cultivar of Mini *Impatiens* plant named 'Bodlizsal', as illustrated and described.

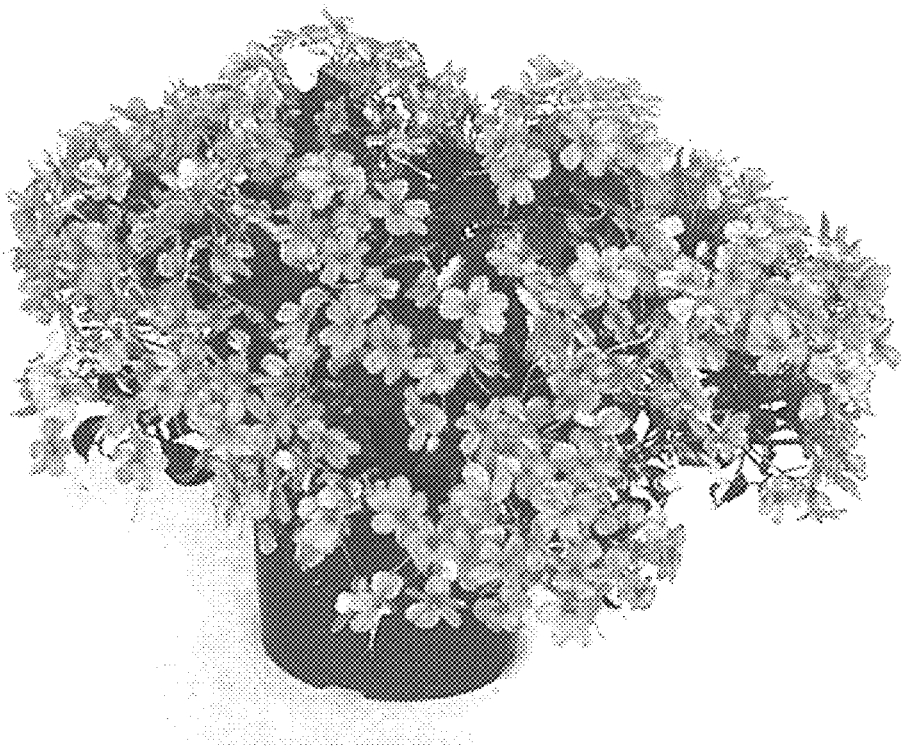
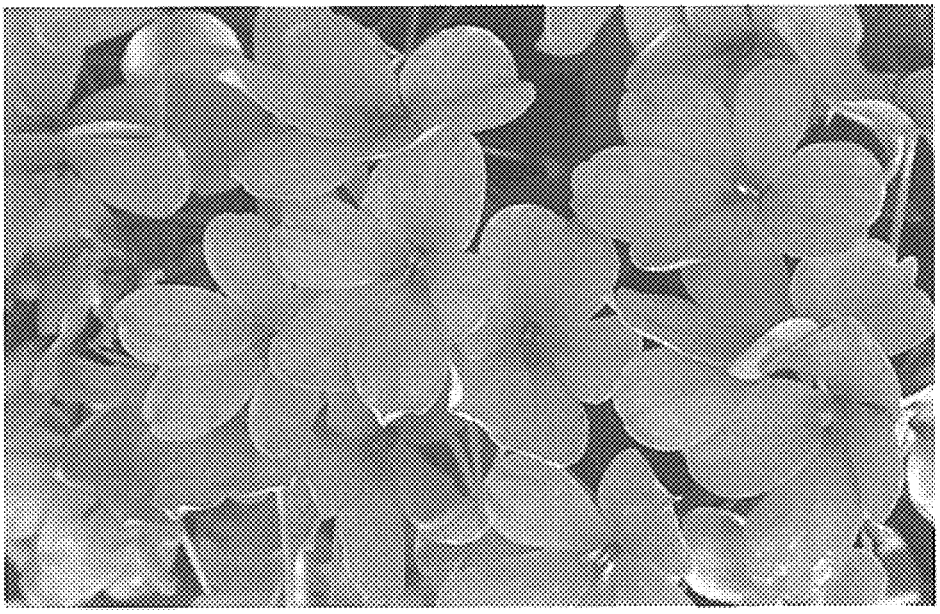

* * * * *